United States Patent [19]
Mark

[11] Patent Number: 5,949,536
[45] Date of Patent: Sep. 7, 1999

[54] HIGH PRESSURE OPTICAL CELL FOR SPECTROMETRY

[76] Inventor: Howard L. Mark, 21 Terrace Ave, Suffern, N.Y. 10901

[21] Appl. No.: 08/840,376

[22] Filed: Apr. 29, 1997

Related U.S. Application Data

[60] Provisional application No. 60/039,834, Mar. 3, 1997.

[51] Int. Cl.$^6$ ..................................................... G01N 15/02
[52] U.S. Cl. ........................................... 356/246; 250/428
[58] Field of Search .............................. 356/246; 250/428

[56] References Cited

U.S. PATENT DOCUMENTS

| | | |
|---|---|---|
| 3,370,502 | 2/1968 | Wilks, Jr. . |
| 4,565,448 | 1/1986 | Abbott et al. ............................ 356/246 |
| 4,595,833 | 6/1986 | Sting . |
| 4,614,428 | 9/1986 | Harris et al. . |
| 4,988,195 | 1/1991 | Doyle . |
| 5,003,174 | 3/1991 | Dätwyler et al. . |
| 5,124,555 | 6/1992 | Härtl . |
| 5,220,401 | 6/1993 | Milosevic et al. . |

OTHER PUBLICATIONS

Whyman et al., A high–pressure spectroscopic cell for FTIR measurements, J. Phys. E: Sci. Instrum., vol. 17, Jul. 1984.
Liquid Transmission Sampling: "Zero Dead volume Flow–Thru Cell" (3M).
Taking the Spectroscopy of Fluids Beyond the Limits: "Advances in Sampling at High Temperatures and Pressures" by Valentine J. Rossiter, Spectroscopy 10(6) Jul./Aug. 1995 (pp. 18–21).

The Review Of Scientific Instruments, vol. 41, No. 12, Dec., 1970: "A Window Configuration For High Pressure Optical Cells" by H.S. Stromberg and R.N. Schock, University of California, Lawrence Radiation Laboratory, Livermore, CA, pp. 1880–1881.
Applied Spectroscopy, vol. 48, No. 8, 1994, pp. 1030–1032: "New Fiber–Optic–Based High–Pressure Cell for Fluorescence Measurements in Near– and Supercritical Solvents" by Jeanette K. Rice, Richard A. Dunbar, and Frank V. Bright.
Analytical Chemistry, vol. 66, No. 20, Oct. 15, 1994, pp. 3543–3551, "Simple Fiber–Optic Interface For On–Line Supercritical Fluid Extraction Fourier Transform Infrared Spectrometry" by D.L. Heglund and D.C. Tilotta, Dept. of Chem., Univ. of North Dakota, Grand Forks, ND; and S.B. Hawthorne and D. J. Miller, Energy & Enviromental Research Center, Univ. of North Dakota, Grank Forks, ND.
Applied Spectroscopy, vol. 51, No. 3, 1997, "New High–Pressure Fiber–Optic Cell for Time–Resolved Emission and Absorbance Measurements in Near– and Supercritical Solvents", by T.A. Rhodes, et al.

*Primary Examiner*—Robert H. Kim
*Assistant Examiner*—Zandra V. Smith
*Attorney, Agent, or Firm*—St. Onge Steward Johnston & Reens LLC

[57] ABSTRACT

A high pressure optical cell for spectrometry is provided. The cell includes a monolithic crystal having a longitudinal bore within. The cell also includes a sheath/housing for holding monolithic crystal and sample introduction tubes. The sample introduction tubes can be microwelded. Compression ferrules or O-rings are used for sealing. A method for making the cell is also provided. A spectroscopic analyzer having a high-pressure optical cell is further provided.

7 Claims, 2 Drawing Sheets

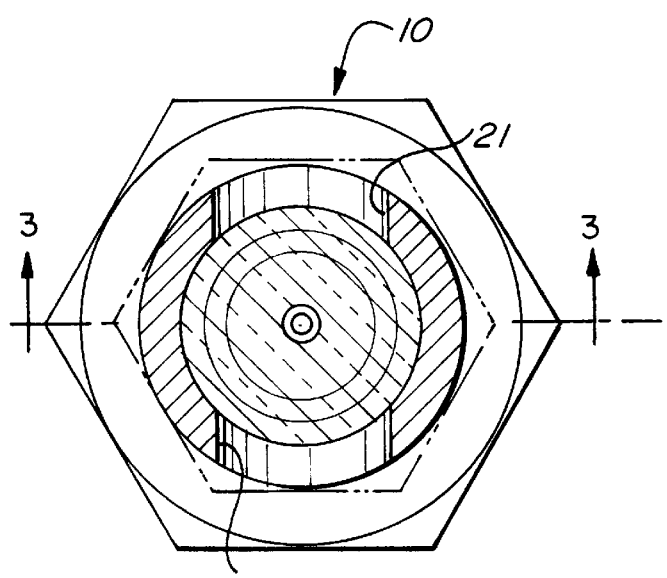
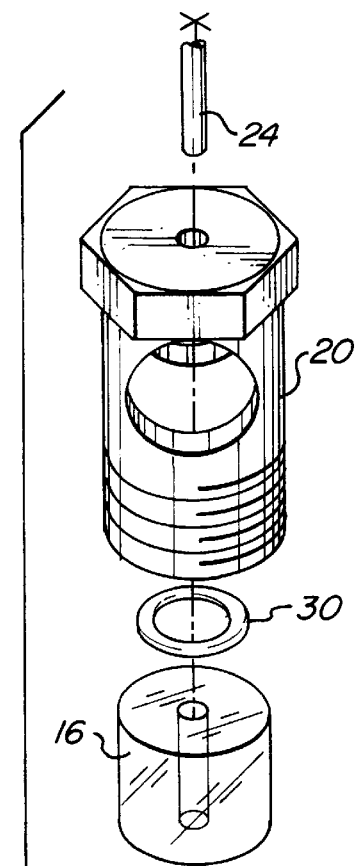
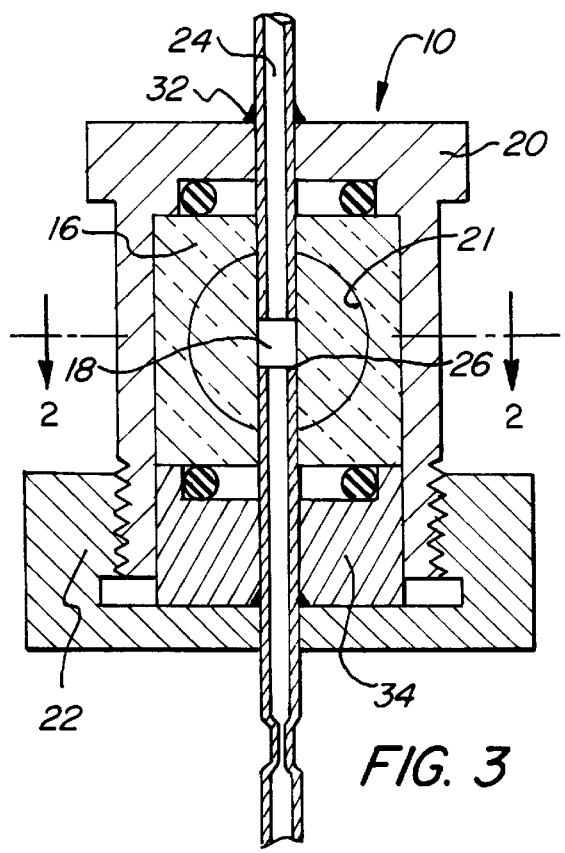
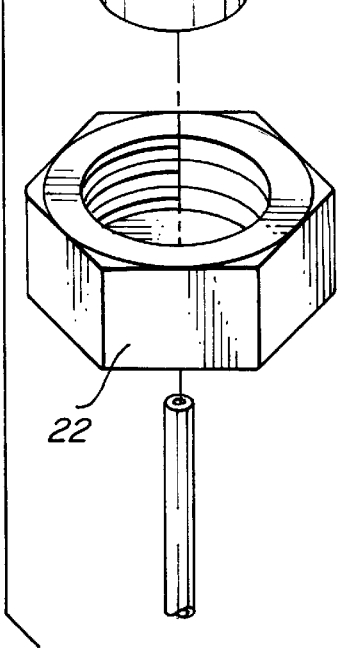

HIGH PRESSURE OPTICAL CELL FOR SPECTROMETRY

This is a continuation of my prior pending provisional application Ser. No. 60/039,834, filed Mar. 3, 1997.

FIELD OF THE INVENTION

The invention relates to a high-pressure optical cell for spectroscopic analyzers, and more specifically to a high-pressure optical cell for in-line chemical analysis.

BACKGROUND OF THE INVENTION

Optical cells for in-line spectroscopic analysis of chemical samples is important for the chemical process industry. In-line spectroscopic analysis enables the real-time determination of chemical content and concentration of chemical samples (i.e., qualitative and quantitative analysis) as the chemical is being generated or used in the chemical process.

Spectroscopic analyzers typically utilize optical cells, an apparatus for introducing a chemical sample into the cell, a light source shining on the cell, and data collection and analysis instrumentation. Optical cells are available for use with various light sources, sample types, sample introduction methods, and collection and analysis modules. Optical cells are typically used for off-line batch sample analysis, but in-line optical analysis cells having limited performance characteristics also exist. Optical cells are designed for gaseous and liquid sample analysis.

Optical cells are used to hold the sample adjacent to the optical source allowing analysis of the chemical sample. The prior art optical cells typically use windows comprising the light transmitting material sealed to a pressure resistant housing. This configuration of the prior art cells may leak, especially at high-pressures, soiling and/or damaging instruments, skewing test results, and/or necessitating time consuming cell cleanup.

U.S. Pat. No. 3,370,502 (Wilks), U.S. Pat. No. 4,595,833 (Sting), U.S. Pat. No. 4,988,195 (Doyle), U.S. Pat. No. 5,220,401 (Milosevic) disclose cylindrical rod-shaped multiple internal reflection elements having various end-shapes for improved optical transmission. They contemplate external sample chambers defined by a housing and the rod-shaped cylindrical optical transmitting members. For each of these inventions, the sample is introduced around the rod-shaped optical crystal. Wilks includes an adjustable housing for adjusting the sample area. For each of these inventions, the sample chamber is defined using multiple pieces that can allow the sample material to leak, especially at high pressures.

U.S. Pat. No. 4,614,428 (Harris), U.S. Pat. No. 5,003,174 (Datwyler), and U.S. Pat. No. 5,124,555 (HartI) disclose windows comprised of optical transmitting members. Further, this art teaches multiple piece sample chambers. In addition, Harris, Datwyler and HartI teach sample chambers defined by optical windows and the cell housing. Harris includes a two-piece cell and two optical transmitting members defining a sample chamber. Datwyler discloses an internal sample chamber defined by the cell and two optical windows inserted in opposing ends of the cell. HartI discloses an optical disc-shaped window having a flat circular measurement surfaced formed by rounding or cutting a conical shape into a flat optical disc material. The internal sample chamber in HartI is defined by using two rounded windows and the cell housing. Other such conically-shaped, window cell designs are known in the art and disclosed in Stromberg, H. D., Schock, R. N., "A Window Configuration for High Pressure Optical Cells", Review of Scientific Instruments, Vol. 41, No. 12 (December 1970).

Optical fiber light transmitting members used in cells are known in the art. Rice, Jeanette K., et al., in "New Fiber-Optic-Based High-Pressure Cell for Fluorescence Measurements in Near- and Supercritical Solvents," Applied Spectroscopy, Vol. 48, No. 8 (1994), pp. 1030–32, and Heglund et. al. In "Simple Fiber-Optic Interface for On-Line Supercritical Fluid Extraction Fourier Transform Infrared Spectrometry," Analytical Chemistry, Vol. 66, No. 20 (Oct. 15, 1994), pp. 3543–51 disclose a typical fiber optic configuration. In this configuration, a stainless steel cross-shaped cell and the optical fiber define the internal sample chamber. The optical fiber passes axially through one axis of the cross; the sample fluid passes through the opposing axes of the cross surrounding the optical transmitting member.

A disadvantage of the prior art is that sample fluids can leak from the cells. This occurs because it is difficult to achieve a leak-free seal between metal cell-housings and the optical transmitting materials used in the art. While in some cases fused seals are used for leak free operation, these applications are limited to either batch measurement or have the added disadvantage of having dead volume, and/or not being readily reusable due to the time and expense of cleaning. Thus, leak-free in-line high-pressure analysis is limited with the cells known in the art.

An additional disadvantage of the prior art is that cells known in the art comprise numerous parts, and are bulky and complex. These parts include at least two optical crystalline material windows, two-piece adjustable housings, and two-piece fused cells. This abundance of parts increases the possibility of leaking, especially at high pressures.

What is desired, therefore, is an optical cell for reliable use at high pressure in spectroscopic analyzers which is low-cost, relatively easy to assemble and clean, and minimizes dead zone.

SUMMARY OF THE INVENTION

Accordingly, it is an object of the invention to provide a spectroscopic cell for relatively leak-free operation at high pressures.

Another object of the invention is to provide a cell for a spectroscopic analyzer that minimizes the number of parts used to makeup the sample chamber, and that is easy to clean.

Still another object of the invention is to provide a cell of the above character that includes a monolithic crystalline sample chamber.

Yet another object of the invention is to provide a cell using a monolithic crystal that includes an internal sample chamber and connecting tubing that is introduced internally into the monolithic crystal defining the internal chamber with reduced dead volume.

A further object of the invention is to provide a cell of the above character which includes a sheath for balancing the forces applied to the crystal forming the sample chamber.

In further aspects, it is other objects of the invention to provide a method of making spectroscopic cells of the above character, and to provide a spectroscopic analyzer including a cell of the above character.

BRIEF DESCRIPTION OF THE DRAWINGS

FIG. 1 is an exploded isometric view of one embodiment of the cell in accordance with the invention;

FIG. 2 is a top sectional view of the cell of FIG. 1 taken along the plane 2—2;

FIG. 3 is a side cross sectional view of the cell of FIG. 2 taken along the plane 3—3;

DETAILED DESCRIPTION OF THE INVENTION

Figure 4:
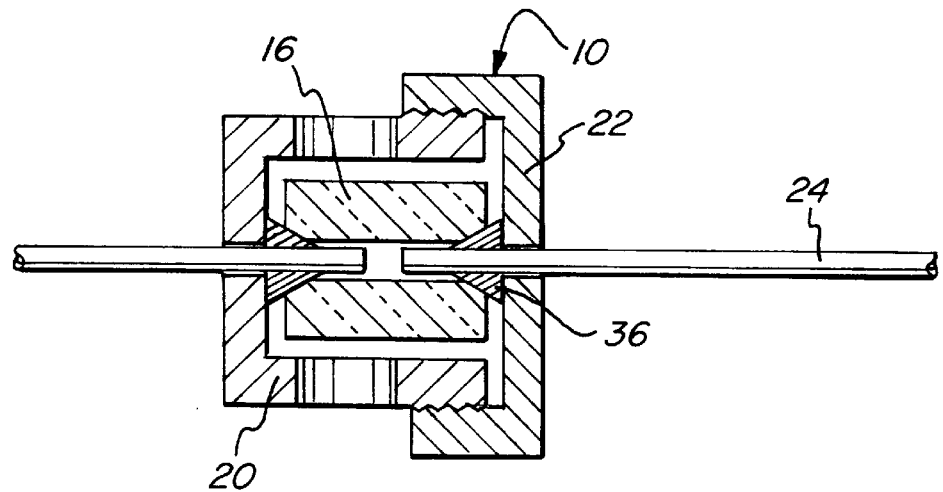
FIG. 4 is a side cross sectional view of another embodiment of the cell in accordance with the invention.
Figure 5:
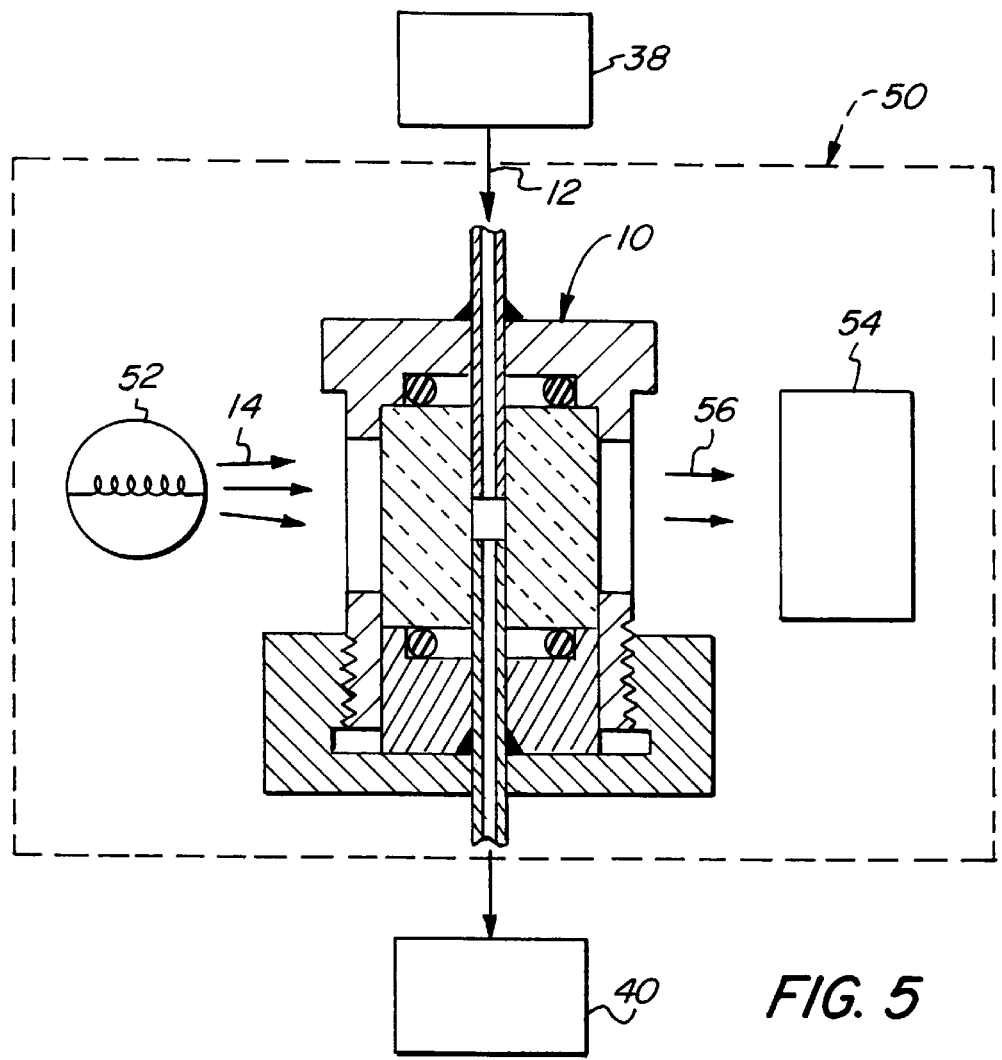
FIG. 5 is a schematic view of a spectroscopic system utilizing the cell of FIG. 1.

FIGS. 1–5 depict an optical cell 10 in accordance with the present invention for spectroscopic analysis of a sample 12 (see FIG. 5). In the use of these cells for spectrometers 50, infrared analysis is the most common light beam 14 used, however, it is understood that other types of light sources 52 may be used.

Referring now to FIG. 3, the cell 10 includes a monolithic crystal 16 with an internal sample chamber 18 and held within a housing/sheath 20 and a cap 22. Internal sample chamber 18 can be formed when monolithic crystal 16 is grown, or can be drilled longitudinally within monolithic crystal 16. While the FIGS. 1-5 depict a screw cap 22 for holding the monolithic crystal 16, it is understood that other components, such as clamps, may be used to hold the crystal in longitudinal compression with respect to axis X (see FIG. 1) within the housing 20. The housing 20 includes a pair of windows/cutouts 21 for introducing light beam 14 and for analyzing at 54 the beam 56 generated by interaction with the sample (see FIG. 5).

FIG. 5 shows the invention in use as part of a spectrometer. A light source 52 is introduced adjacent to the window 21. The light beam 14 enters the sample and a portion is transmitted through the monolithic crystal 16 and interacts with the sample in sample chamber 18 and exits through the other window to a light sample analysis portion 54 of a spectrometer 50.

Sample introduction tubes 24 are disposed within the monolithic crystal 16 through the housing 20 directly opposite each other. The space between the opposing sample introduction tube ends 26 provides a sample chamber 18 with a reduced dead zone. The sample is introduced in the sample inlet 38 and can exit through the sample exit 40. The sample introduced in the sample inlet 38 can be prepared, such as by using a gas chromatograph or liquid chromatograph. The sample exit 40 can return to a process in the case of inline analysis. The tube ends 26 can be modified to facilitate cleaning sample chamber 18, such as by flaring out the tube ends 26. o-rings 30 disposed at opposite ends of monolithic crystal 16 seal crystal 16 and housing 20. While Teflon o-rings may be used, it is understood that o-rings of other materials, such as neoprene, depending upon the compatibility between the chemical sample and o-ring at the test conditions (i.e., temperatures and pressures).

In one embodiment in accordance with the present invention, a microweld 32 is used to seal the sample tubes 24 to cap insert 34 and the housing 20 (see FIG. 3). It is preferred that microweld 32 is on the outside of sample tubes 24, cap insert 34 near the inside edge of cap 22, and housing 20 ensuring that o-ring 30 effectively seals crystal 16 and housing 20. In yet another embodiment in accordance with the present invention as shown in FIG. 4, a compression ferrule 36 is used, without a micro-weld, to seal the sample tubes 24 directly to the monolithic crystal with cap 22. It is understood that microwelding is a type of welding, and includes brazing.

It is preferred that the monolithic crystal is made of sapphire. It is understood, however, that optical elements including fiber-optic materials, NaCl, synthetic (e.g., zirconia), natural diamond, ZnS, Ge, Si, sapphire, AgBr, AgCl, KRS-5, HDPE, and ZnSe may be used.

Cell 10 can be manufactured by heating metallic housing/sheath before placing it over the crystal so that when the housing/sheath cools, it holds the crystal therein in radial compression with respect to axis X. The addition of the screw cap to hold the crystal in longitudinal compression with respect to axis X offsets the radial compression which is a tension force in the longitudinal direction. This balance of forces on the crystal improves the cell's ability to retain high pressure samples without significant leaking.

Although the invention has been described with reference to a particular arrangement of parts, features and the like, these are not intended to exhaust all possible arrangements of features, and indeed many other modifications and variations will be ascertainable to those of skill in the art.

What is claimed is:

1. A spectroscopic cell comprising:

a monolithic light-transmitting cylindrical/spherical crystal having a longitudinal bore;

a tubular housing/sheath for holding said monolithic crystal therein, said tubular housing having at least two cutout/windows in its midsection for allowing light to transmit through said crystal;

a cap adjustably connectable to said sheath for holding said crystal in longitudinal compression in said housing; and two sample introduction tubes located within said crystal bore to reduce dead zone and define a sample chamber, one of said tubes being sealed to said housing and the other of said tubes being sealed to said cap, said cap sealing said tubes to said crystal.

2. The cell for a spectroscopic analyzer of claim 1, wherein the sample introduction tube is micro-welded to said housing/sheath and cap insert juxtaposed between cap, and o-ring and crystal.

3. The cell for a spectroscopic analyzer of claim 1, wherein the sample introduction tube includes ferrules for seating on sealing surfaces of the crystal bore.

4. A method of making a spectroscopic cell comprising the steps of:

providing a monolithic crystal;

drilling a hole in the crystal to form a sample chamber;

heating a sheath and placing it over an outer surface of the crystal so that it will apply radially inward pressure to the crystal as it cools; and mounting a cap including a sample introduction tube to place the crystal in longitudinal compression with the tube in the hole.

5. A spectroscopic analyzer comprising:

a monolithic light-transmitting cylindrical/spherical crystal having a longitudinal bore;

a tubular housing/sheath for holding said monolithic crystal therein, said tubular housing having at least two cutouts/windows in its midsection for allowing light to transmit through said crystal;

a cap adjustably connectable to said sheath for holding said crystal in longitudinal compression in said housing; and two sample introduction tubes located within said crystal bore to reduce dead zone and define a sample chamber, one of said tubes being sealed to said housing and the other of said tubes being sealed to said cap, said cap sealing said tubes to said crystal.

6. A spectroscopic cell as in claim 1 wherein said housing/sheath is sized so as to hold said monolithic crystal in radial compression therein.

7. A spectroscopic analyzer as in claim 5 wherein said housing/sheath is sized so as to hold said monolithic crystal in radial compression therein.

* * * * *